United States Patent [19]

Buster et al.

[11] Patent Number: 4,816,257

[45] Date of Patent: Mar. 28, 1989

[54] METHOD FOR PRODUCING AN IN VIVO ENVIRONMENT SUITABLE FOR HUMAN EMBRYO TRANSFER

[75] Inventors: John E. Buster, Rancho Palos Verdes, Calif.; James A. Simon, Norfolk, Va.

[73] Assignee: Research & Education Institute, Harbor-UCLA Medical Center Inc., Torrance, Calif.

[21] Appl. No.: 92,069

[22] Filed: Sep. 2, 1987

Related U.S. Application Data

[63] Continuation of Ser. No. 778,559, Sep. 20, 1985, abandoned.

[51] Int. Cl.$^4$ .................... A61K 9/00; A61K 31/56
[52] U.S. Cl. ................... 424/430; 604/890.1; 514/170; 514/899; 514/967; 424/431; 424/432; 600/34; 600/33
[58] Field of Search ................ 424/430–433; 514/899, 967, 170; 128/130; 604/890

[56] References Cited

U.S. PATENT DOCUMENTS

| | | | |
|---|---|---|---|
| 3,545,439 | 12/1970 | Duncan | 128/130 |
| 3,656,483 | 4/1972 | Rudel | 128/130 |
| 3,755,575 | 8/1973 | Lerner | 514/170 |
| 3,845,761 | 11/1974 | Zaffaroni | 128/130 |
| 3,896,819 | 7/1975 | Zaffaroni | 128/130 |
| 3,957,982 | 5/1976 | Lachnit-Fixson et al. | 514/170 |
| 4,071,623 | 1/1978 | Van der Vies | 514/170 |
| 4,091,028 | 9/1981 | Vorys | 514/899 |
| 4,323,548 | 4/1982 | Scherm | 514/967 |
| 4,425,339 | 1/1984 | Pitchford | 514/170 |
| 4,439,432 | 3/1984 | Peat | 514/899 |
| 4,551,148 | 11/1985 | Riley et al. | 514/967 |

FOREIGN PATENT DOCUMENTS

2034182 6/1980 United Kingdom .

OTHER PUBLICATIONS

Lutjen, P., et al, "The Establishment and Maintenance of Pregnancy Using *In Vitro* Fertilization and Embryo Donation in a Patent with Primary Ovarian Failure," *Nature*, 307, 174 (1984).

Bustillo, M. et al., "Nonsurgical Ovum Transfer as a Treatment in Infertile Women: Preliminary Experience," *J. Amer. Med. Assoc.* vol. 251, No. 9, 1171 (1984).

Hodgen, G. D., "Surrogate Embryo Transfer Combined with Estrogen–Progesterone Therapy in Monkeys," *J. Amer. Med. Assoc.*, 250, 2167 (1983).

Folkman, J., et al, "The Use of Silicone Rubber as a Carrier for Prolonged Drug Therapy", *J. Surg. Res.*, 4, 139 (1964).

Kind, F. A., et al, "Sustained Release Hormonal Preparations," *Acta Endrocinol. Suppl.* (Copenh.), 151, 55:5 (1971).

Hunter, D. J. S., et al, "Plasma Levels of Estrogen, Luteinizing Hormone and Follicle Stimulating Hormone Following Castration and Estradiol Implant," *Obstet. Gynecol.*, 49, 180 (1977).

Loeper, J., et al, "The Influence of Estrogen Therapy on Triglycerides: Importance of the Choice of Substance and Route of Administration," *Nouv. Presse Med.* 6, 2747 (1977).

Whitehead, M. I., et al, "Adsorption and Metabilism of Oral Progesterone," *Br. Med. J.*, 280, 825 (1980).

Nillius, S. J., et al, "Plasma Levels of Progesterone After Vaginal, Rectal or Instramuscular Administration of Progesterone," *Am. J. Obstet. Gynecol.*, 110, 470 (1971).

Katz, Z., et al, "Teratogenicity of Progestogens Given During the First Trimester of Pregnancy," *Obstet. Gynecol.* 65, 775 (1983).

(List continued on next page.)

*Primary Examiner*—Ronald W. Griffin
*Attorney, Agent, or Firm*—Drucker & Sommers

[57] ABSTRACT

A method for producing, in a functionally agonadal human female body, an environment suitable for the implantation, nutrition, and development of an embryo, comprising the placement of at least one carrier containing at least one releasable steroid hormone into the vagina of the human female.

18 Claims, 1 Drawing Sheet

OTHER PUBLICATIONS

Resseguie, L. J., et al, "Congenital Malformations Among Offspring Exposed in Utero to Progestins, Olmsted County, Minnesota, 1936-1974," *Fertil. Steril.*, 43, 514 (1985).

Mishell, D. R., "Absorption of Steroids ThroughSilastic in Animals and Humans-Results of Studies in Humans," *Advances in Planned Parenthood*, 5, 151 (1970).

Sivin, I., et al, "A Multicenter Study of Levonorgestrel-estradiol Contraceptive Vaginal Rings. I. Use Effectiveness. An International Comparative Trial," *Contraception*, 24, 341 (1981).

Mishell, D. R. et al, "Clinical Performances and Endocrine Profiles with Contraceptive Vaginal Rings Containing a Combination of Estradiol and D-Norgestrel," *Am. J. Obstet. Gynecol.*, 130, 55 (1978).

Toivonen, J., "Pituitary and Gonadal Function During the use of Progesterone-or Progesterone-estradiol-releasing Vaginal Rings," *Int. J. Fertil*, 25, 106 (1980).

Mishell, D. R. et al, "Inhibition of Ovulation With Cyclic Use of Progesten-Impregnated Intravaginal Devices," *Am. J. Obstet. Gynecol.*, 113 927 (1972).

Johansson, E. D. B. et al, "The Effect of Progestin R2323 Released From Vaginal Rings on Ovarian Function," *Contraception*, 12 299 (1975).

Mishell, D. R. et al, "Contraception By Means of a Silastic Vaginal Ring Impregnated With Medroxyprogesterone Acetate," *Contraception* 107, 100 (1970).

Mishell, D. R., et al, "Contraceptive Effect of Varying Dosages of Progestogen in Silastic Vaginal Rings," *Fertil. Steril*, 21, 99 (1970); and Mishell, Footnote 13, infra.

Stumpf, P. G., et al, "Development of a Vaginal Ring for Achieving Physiologic Levels of 17b-estradiol in Hypoestrogenic Women," *J. Clin. Endocrinol. Metab.*, 54, 208 (1982).

Yen, S. S. C., et al, "Circulating Estradiol, Estrone and Gonadotropin Levels Following the Administration of Orally Active 17b-estradiol in Postmenopausal Women," *J. Clin. Endocrinol. Metab.*, 40, 518 (1975).

Langren, B. M. et al, "Hormonal Profile of the Cycle in 68 Normally Menstruating Women," *Acta Endocrinologica* 94, 89 (1980).

Csapo, *Am J. Obstet. Gynecol.* 115. 759 (1973).

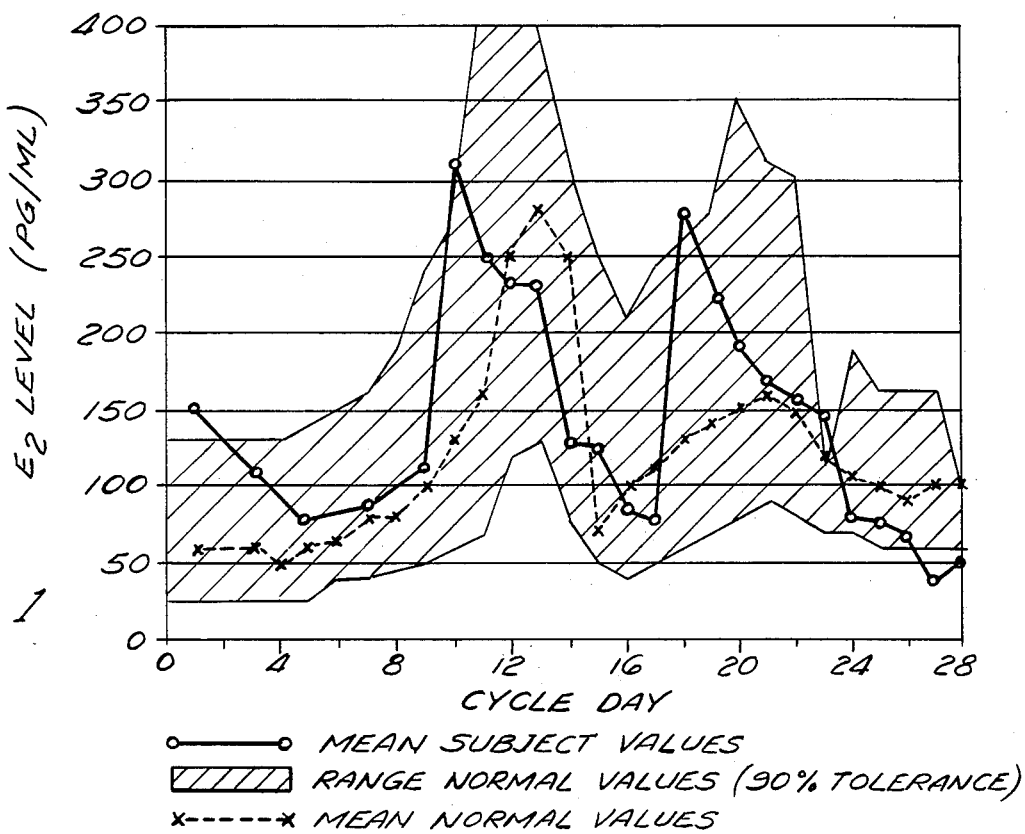
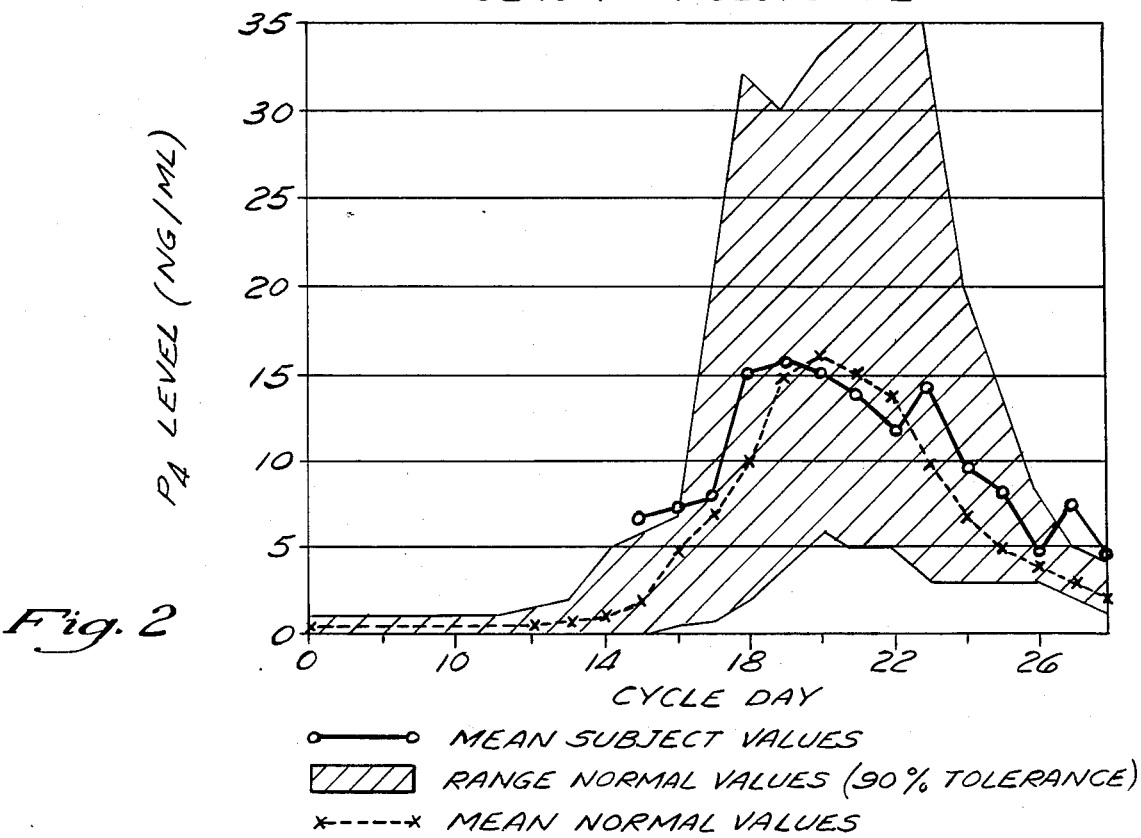

METHOD FOR PRODUCING AN IN VIVO ENVIRONMENT SUITABLE FOR HUMAN EMBRYO TRANSFER

This application is a continuation of application Ser. No. 778,559, filed 9-20-85 now abandoned.

BACKGROUND OF THE INVENTION

Many women are infertile, due to surgical removal of their ovaries, premature ovarian failure, exposure to ionizing radiation, toxic chemicals, or drugs, or because of ovaries that have not developed properly, or never developed at all (these women are sometimes hereinafter referred to generally as "functionally agonadal."). Additionally, some women have abnormally low production of hormones, which require exogenous supplemention in order to prevent infertility or early miscarriages.

Various treatments for functionally agonadal women have been developed, including in-vitro fertilization, where the oocyte of a donor is surgically removed from the body, fertizied in a laboratory vessel (in-vitro), and then the fertilized ovum is non-surgically placed into the uterus of the "recipient" woman.[1] Additionally, nonsurgical ovum transfer is a recent treatment for these functionally agonadal, infertile, women, involving the nonsurgical recovery of an in vivo fertilized human ovum from a fertile donor, and its nonsurgical transfer to an infertile recipient women.[2] Prior to the availability of these donor procedures, there was no possibility of a functionally agonadal woman becoming pregnant.

Previously, an essential step in any of these embryo transfer processes has been the matching of an ovum recipient with a donor who ovulates at about the same time, because the steroid hormone levels in their bloodstreams must be at about the same level for the recipient's body to accept the transfer. Synchronizing ovulation is a complicated procedure, often achieved by having the recipient woman take oral contraceptives and the like. For recipient women whose bodies produce abnormal or insufficient levels of the steroid hormones required for the implantation and proper development of an embryo, some steroid hormone replacement or augmentation is essential if they are to successfully carry the embryo until the pregnancy reaches the luteal-placental shift (i.e. a level of development where the pregnancy itself makes the requisite hormones).

Prior efforts to supply physiologic hormone levels, to women having inadequately low endogenous hormones, or to functionally agonadal women desirous of undergoing an embryo transfer, using various steroid hormone delivery systems, have had significant disadvantages, and may contribute to low efficiency.[3] For example, subcutaneous implants for delivery of steroid hormones require surgical insertion and removal, and may provoke deposition of fibrous tissue and alter hormone release rates.[4] Crystalline pellets require surgical insertion and are difficult to remove if side effects develop.[5] Dermatologic creams,[6] intranasal solutions,[7] oral[8] or sublingual tablets,[9] intramuscular injections and vaginal or rectal suppositories,[10] all result in bolus delivery (i.e. a single massive dose) rather than sustained serum levels, and many of these involve messy, inconvenient, or painful delivery.

The physician's therapeutic alternatives for simulation or augmentation of the luteal phase are also limited. Progesterone does not have sufficient activity when given orally, and while still controversial,[11] there appear to be congenital anomalies associated with first trimester administration of synthetic orally active progestins. Thus, the physician's choices appear to be limited to intravaginal and/or intrarectal progesterone suppositories, and intramuscular injections of progesterone in oil.

Silicone rubber (or polysiloxane) has been found to be useful in chronic implants in tissue because it does not cause rejection reactions, even after prolonged periods. It is further known in the art that certain drugs, when incorporated into a device made of polysiloxane, will pass through the polysiloxane carrier and into saline solutions, and when implanted subcutaneously, or placed within a human female's vagina, these drugs will be absorbed into the bloodstream, with a rate of passage dependent on, among other things, the surface area of the material.[12] Systemic delivery of contraceptive steroids[13] and replacement of low levels of estradiol in postmenopausal women[14] by polysiloxane vaginal rings has been shown.

There has long been a need for a practical method for establishing physiologic levels of estrogen and progesterone to women with abnormal menstrual cycles, and to functionally agonadal women in order to facilitate donor embryo transfer, which would avoid the vagaries of oral absorption,[15] the effects of oral administration on liver proteins due to initial portal circulation,[16] the use of synthetic hormones which have been associated with birth defects,[17] and the inconvenience of intramuscular injections.

SUMMARY OF THE INVENTION

It is therefore an object of this invention to overcome some of the problems of the prior art, by providing a method for producing, in a functionally agonadal human female, an environment suitable for the implantation, nutrition, and development of an embryo, comprising the placement of at least one carrier material, either solid, gel, or cream, containing at least one releasable steroid hormone therein, within the vagina of a human female.

BRIEF DESCRIPTION OF THE DRAWINGS

FIG. 1 illustrates four cuves correlating mean serum estradiol levels in subjects utilizing the method of this invention through a twenty-eight day cycle, with serum estradiol levels in normally menstruating women.

FIG. 2 illustrates four curves correlating mean serum progesterone levels in subjects utilizing the method of this invention through a twenty-eight day cycle, with serum progesterone levels in normally menstruating women.

DETAILED DESCRIPTION OF THE INVENTION

As described generally above, this invention relates to a method for simulating, in vivo, the steroid milieu of the normal human female ovulatory menstrual cycle, and of early phase (i.e. first trimester) pregnancy. Hormonal profiles of the menstrual cycle in normally meenstruating women are shown in FIGS. 1 and 2, where the shaded areas represent 90% tolerance limits, covering 90% of the population with 90% probability, and geometric mean values for 68 normally menstruating women are indicated by the X's.[18] In the "normal" follicular phase, mean 17-beta-estradiol values range from 50 pg/ml to approximately 300 pg/ml; in the same phase, mean progesterone levels are less than 1 ng/ml. In the "normal" luteal phase, mean estradiol values range from 50 pg/ml to approximately 200 pg/ml, and mean progesterone values range from 4 ng/ml to 30 ng/ml.

The method of this invention utilizes a device comprised of a solid carrier, or a carrier of a gel-like or creamy consistency, impregnated with estrogen and progesterone, to be placed within the vagina of a human female, to provide: (1) continuous and sustained hormone release leading inter alia, to a morphologically and endocrinologically "normal" endometrium, (2) serum levels of particular steroid hormones within the normal range of an entire menstrual cycle as well as an early stage of pregnancy, and (3) a convenient and physiologic therapeutic alternative to oral, vaginal, or intramuscular steroid replacement in human females undergoing donor embryo transfer.

The presently preferred carrier material is a solid silicone elastomer, polysiloxane, although other suitable materials, such as polyethylene glycol, of a creamy consistency, may be utilized. The devices utilized in this invention may be prepared, according to the presently preferred embodiment, by mixing the desired steroid hormone (preferably crystalline 17-beta-estradiol ($E_2$) and/or cyrstalline progesterone ($P_4$)) into fluid polysiloxane which may then be activated by stannous octoate, injected under pressure into acrylic polymer molds, polymerized according to previously known methods at 70° C. for twelve hours, removed from the molds, trimmed and gas sterilized for use.

The steroid hormones are released from the carriers by the action of the bodily fluids which come into contact with the carrier, it is presently believed.

Various shapes for the carrier are emcompassed within the spirit of this invention, including carriers that are custom molded to fit a particular user's requirements. It is presently preferred to utilize solid carriers that are ring shaped and/or generally cylindrical, or tampon-shaped, and to utilize a sequence of different devices incorporating varying amounts of steroid hormones to simulate varying physiologic levels.

The carriers or devices that are ring shaped are placed into a human female user's vagina, and positioned around the cervix (with the anterior portion fitting behind the pubic symphysis, and the posterior portion of the ring fitting behind Douglas' cul-de-sac). The carriers of other shapes are inserted into the vagina. These carriers may be removed for brief periods of approximately a few hours or less, and reinserted, without resulting in any decline in blood hormone levels. The carriers may be removed at the end of a "normal" menstrual cycle, to permit blood hormone levels to decline to the physiologically normal levels that permit the onset of menstruation.

To simulate a "normal" human female menstrual cycle, it is presently preferred to utilize a sequence of rings and tampons, with the size and formulation characteristics set forth in Table 1 below. Other size and formulation characteristics may be desirably chosen to suit a particular user's requirements.

TABLE 1

| Device | Ring and Tampon size and Formulation Characteristics | | | | |
|---|---|---|---|---|---|
| | Steroid Formulation | R (cm)* | r (cm)* | Length (cm) | Surface Area (cm$^2$) |
| Ring I | 200 mg $E_2$ | 2.3 | 0.40 | | 36.3 |
| Ring II | 400 mg $E_2$ | 2.3 | 0.44 | | 39.9 |
| Ring III | 400 mg $E_2$ + 1000 mg $P_4$ | 2.3 | 0.44 | | 39.9 |
| Tampon | 2000 mg $P_4$ | 1.25 | 0.75 | 8 | 62.8 |

*R = outer radius, r = inner radius

A study has been done, by the applicants in collaboration with their technical coworkers (Simon et al. "Polysiloxane Vaginal Rings for Physiologic Endometrial Priming in Functionally Agonadal Women," 1985, to be published), using the method of this invention to produce normal hormonal levels in functionally agonadal women, the results of which are set forth below, by way of example.

EXAMPLE

Five functionally agonadal women ages 28–40 years participated in the study. Four had premature ovarian failure, and one had been sugically castrated because of severe endometriosis. All had menopause documented by amenorrhea of more than one year duration, atrophic vaginal and cervical cytology and repeated serum FSH levels in excess of 40 mIU/ml.

Polysiloxane vaginal rings and tampons were utilized, prepared as set forth, infra in this application.

Ring I was placed in the vagina on simulated cycle day 1 and removed on day 11 when Ring II was substituted for it. On cycle day 14 Ring I was substituted for Ring II and was continued in place until cycle day 19, when Ring III was substituted. ON cycle day 25, Ring I was substituted for Ring III, and Ring I was continued in place until cycle day 28. During cycle days 15 to 28 a progesterone containing polsiloxane tampon was added to the regimen to provide mid-luteal phase progesterone levels. Subjects changed rings and tampons between 0700 and 0900 hours on the indicated days. All subjects kept a daily diary of routine activities and untoward symptoms related to the rings or tampons. They all underwent routine venipunctures between 1400 and 1700 hours on the cycle days, 1, 3, 5, 7, 9, 11, and daily thereafter. Serum was separated and stored at −20° C. until assayed.

All serum samples were assayed in a single RIA for either estradiol or progesterone using commercially available direct RIA kits, using $^{131}$I-labelled hormones. The direct assays had been validated and the results correlated with previously described assays utilizing extraction (Estradiol: N=71, r=0.9907, y=0.9783x+0.6737; Progesterone: N=34, r=0.9804, y=0.9705x+0.1078).

On cycle day 26, endometrial tissue from the fundal portion of the uterus was collected transcervically under paracervical anesthesia. This tissue was either "snap" frozen in liquid nitrogen and stored at −70° C. until assayed for total $E_2$ and $P_4$ receptor content, using methods well known in the art, or fixed in 10% neutral buffered formalin and stained with hematoxylin and eosin for histologic dating according to known methods, or fixed in 2.5% gluteraldehyde and 2% formaldehyde at pH 7.3 for 48 hours, then dehydrated in ascending concentrations of absolute ethanol, critical point dryed and sputter coated with gold paladium according to methods well known in the art. Additionally, scanning electron micrographs of the endometrium on cycle day 26 were taken.

All subjects tolerated the vaginal rings and tampons well, and were able to insert and remove them without difficulty. They uniformly noted a white, odorless, non-irritating vaginal discharge at the beginning of therapy. The discharge consisted of normal appearing mature squamous cells and was compatible with $E_2$ mediated increased vaginal cornification. Some breast discomfort and emotional lability were noted by some of the subjects after the polysiloxane $P_4$ containing vaginal tampon was removed. All subjects had timely withdrawal bleeding. One subject routinely removed the vaginal ring and all subjects removed the tampon temporarily for sexual intercourse. No changes in serum hormone levels could be related to daily activities including bathing, swimming, sexual intercourse, or exercise including horseback riding.

The results from the five subjects during the fourth of four consecutive 28-day treatment cycles are set forth below in Tables 2 and 3, showing serium estradiol and serum progesterone levels, respectively.

TABLE 2

| | Serum Estradiol level (pg/ml) | | | | | | |
|---|---|---|---|---|---|---|---|
| DAYS | E. C. | C. H. | J. M. | K. P. | J. S. | Mean | SEM |
| 1 | 30 | 173 | | 283 | 123 | 152.2 | 22.85 |
| 2 | | | | | | | |
| 3 | 34 | 97 | | 181 | 117 | 107.1 | 13.16 |
| 4 | | | | | | | |
| 5 | 41 | 17 | 122 | 140 | 78 | 79.5 | 9.34 |
| 6 | | | | | | | |
| 7 | 52 | 52 | 98 | 143 | 85 | 86.0 | 6.76 |
| 8 | | | | | | | |
| 9 | 96 | | 120 | 152 | 71 | 109.8 | 7.48 |
| 10 | 111 | 338 | 316 | 473 | | 309.4 | 32.39 |
| 11 | - | 156 | 206 | 405 | 248 | 253.8 | 23.30 |
| 12 | 152 | 166 | 176 | 485 | 186 | 233.0 | 25.30 |
| 13 | 168 | 147 | 213 | 459 | 172 | 231.8 | 23.12 |
| 14 | 104 | 61 | 118 | 189 | 179 | 130.2 | 9.58 |
| 15 | 94 | 73 | 109 | 190 | 166 | 126.3 | 8.87 |
| 16 | | 58 | 87 | 96 | 109 | 87.5 | 4.69 |
| 17 | 60 | 56 | 60 | 152 | 79 | 81.4 | 7.24 |
| 18 | 189 | 218 | 339 | 446 | 250 | 288.4 | 18.69 |
| 19 | 111 | 107 | 171 | 528 | 217 | 226.8 | 31.21 |
| 20 | 184 | 104 | 217 | 304 | 167 | 195.2 | 13.13 |
| 21 | 171 | 93 | 214 | 220 | 149 | 169.4 | 9.30 |
| 22 | 157 | 88 | 154 | 177 | 207 | 156.6 | 7.83 |
| 23 | 161 | 77 | 187 | 189 | 135 | 149.8 | 8.28 |
| 24 | 74 | 36 | 79 | 137 | 78 | 80.8 | 6.46 |
| 25 | 58 | 40 | 69 | 149 | | 79.0 | 10.43 |
| 26 | 42 | 11 | 36 | 170 | | 64.8 | 15.47 |
| 27 | 36 | 19 | 60 | | | 38.3 | 5.61 |
| 28 | 51 | 18 | 51 | 82 | | 50.5 | 5.66 |

TABLE 3

| | Serum Progesterone level (ng/ml) | | | | | | |
|---|---|---|---|---|---|---|---|
| DAYS | E. C. | C. H. | J. M. | K. P. | J. S. | Mean | SEM |
| 7 | 1.0 | 0.5 | 0.3 | 0.4 | 0.7 | | |
| 8 | | | | | | | |
| 9 | 0.8 | 0.2 | 0.3 | 0.3 | 0.7 | | |
| 10 | 0.8 | 0.3 | 0.3 | 0.2 | | | |
| 11 | 0.7 | 0.2 | 0.3 | 0.2 | 0.6 | | |
| 12 | | 0.2 | 0.3 | 0.2 | 0.6 | | |
| 13 | 0.5 | 0.1 | 0.2 | 0.3 | 0.3 | | |
| 14 | 0.5 | 0.1 | 0.4 | 0.2 | 0.5 | | |
| 15 | 8.9 | 3.6 | 7.0 | 8.3 | 6.4 | 6.8 | 0.37 |
| 16 | | 5.3 | 7.6 | 7.6 | 9.1 | 7.4 | 0.34 |
| 17 | 8.0 | 7.5 | 7.5 | 9.4 | 10.0 | 8.5 | 0.21 |
| 18 | 13.0 | 13.3 | 14.0 | 14.8 | 21.0 | 15.2 | 0.59 |
| 19 | 15.0 | 8.6 | 12.5 | 20.0 | 24.0 | 16.0 | 1.09 |
| 20 | 14.0 | 13.3 | 13.0 | 17.0 | 20.0 | 15.5 | 0.54 |
| 21 | 9.0 | 12.0 | 12.5 | 17.0 | 19.0 | 13.9 | 0.72 |
| 22 | 12.0 | 13.0 | 12.0 | 13.0 | 18.0 | 11.6 | 1.05 |
| 23 | 16.0 | 13.1 | 11.0 | 16.0 | 18.0 | 14.8 | 0.49 |

TABLE 3-continued

| | Serum Progesterone level (ng/ml) | | | | | | |
|---|---|---|---|---|---|---|---|
| DAYS | E. C. | C. H. | J. M. | K. P. | J. S. | Mean | SEM |
| 24 | 12.0 | 8.7 | 6.0 | 9.0 | 13.0 | 9.7 | 0.50 |
| 25 | 5.0 | 10.1 | 7.0 | 10.0 | | 8.0 | 0.54 |
| 26 | 4.0 | 2.0 | 4.8 | 7.0 | | 4.5 | 0.45 |
| 27 | 5.0 | 5.6 | 6.0 | | 14.0 | 7.7 | 0.92 |
| 28 | 0.7 | 1.4 | 1.7 | 1.3 | 16.0 | 4.2 | 1.18 |

As shown by the data above, and by the open circles in FIGS. 1 and 2, all of the subjects had $E_2$ and $P_4$ levels within the normal range for spontaneously ovulating women. The $E_2$ levels increased in response to the higher ring content of $E_2$. The serum $E_2$ levels were: mean "midfollicular"—157+/−13 pg/ml (mean+/−SEM), and mean "midcycle" levels of 204+/−21 pg/ml. $P_4$ levels during the "follicular" phase did not exceed 1 ng/ml, but rose to a mean peak "luteal" level of 20+/−2.2 ng/ml with a range of 8.4 to 32 ng/ml. Several subjects had supraphysiologic estradiol levels noted at the beginning of their treatments, but this phenomenon decreased with increased vaginal cornification and prolonged ring use.

The quantities of total $E_2$ and $P_4$ receptors measured in the endometrial biopsy samples responding to stimulation by the polysiloxane one vaginal devices were within the normal range for late luteal phase spontaneously ovulating women, and representative histologic sections, as well as scanning electron micrographs, are compatible with a "normal" cycle, suggesting that the levels of steroid reaching the endometrium were appropriate, and that the uterine epithelium was capable of responding normally.

(END OF EXAMPLE)

The carriers used as part of the methodology of this invention, may be used to establish physiologic levels of steroid hormones sufficient to simulate the "normal" physiologic levels in functionally agonadal human females seeking donor embryo transfer. Additional vaginal carriers would be required after any donor embryo transfer in such a person, until the pregnancy reaches the luteal-placental shift (i.e. a level of development where the pregnancy itself produces all steroid hormones required for its continued maintenance), usually by the seventh week, although the period of support may be extended to twelve weeks.[19]

The method of the present invention may desirably be utilized in part (by utilizing some or all of the carriers) as a convenient and reliable method for treating luteal phase dysfunction in ovulatory women.

The specific shapes and embodiments and methods set forth above are merely illustrative, and may be varied or modified, or different forms or shapes could be used to produce the same desirable results without departing from the scope of the inventive concept.

[1] Lutjen, P., et al, "The Establishment and Maintenance of Pregnancy Using In Vitro Fertilization and Embryo Donation in a Patient with Primary Ovarian Failure," Nature, 307, 174 (1984).

[2] Bustillo, M. et al., "Nonsurgical Ovum Transfer as a Treatment in Infertile Women: Preliminary Experience," J. Amer. Med. Assoc. Vol. 251, No. 9, 1171 (1984).

[3] Hodgen, G. D., "Surrogate Embryo Transfer Combined with Estrogen-Progesterone Therapy in Monkeys," J. Amer. Med. Assoc., 250, 2167 (1983).

[4] Folkman, J., et al. "The Use of Silicone Rubber as a Carrier for Prolonged Drug Therapy, *J. Surg. Res.,* 4, 139 (1964); and Kind, F. A., et al, "Sustained Release Hormonal Preparations," *Acta Endrocinol. Suppl.* (Copenh.), 151, 55:5 (1974).

[5] Hunter, D. J. S., et al, "Plasma Levels of Estrogen, Luteinizing Hormone and Follicle Stimulating Hormone Following Castration and Estradiol Implant," *Obstet. Gynecol.,* 49, 180 (1977).

[6] Loeper, J., et al, "The Influence of Estrogen Therapy on Triglycerides: Importance of the Choice of Substance and Route of Administration," "*Nouv. Presse Med.* 6, 2747 (1977).

[7] Rigg, L. A., et al. "Efficacy of Intravaginal and Intranasal Administration of Estradiol 17b." *J. Clin. Endocrinol. Metab.,* 45, 1261 (1977).

[8] Whitehead, M. I., et al, "Absorption and Metabolism of Oral Progesterone," *Br. Med. J.,* 280, 825 (1980).

[9] Rigg, et al. footnote 8, infra.

[10] Nillius, S. J., et al, "Plasma levels of Progesterone after Vaginal, Rectal or Intramuscular Administration of Progesterone," *Am. J. Obstet. Gynecol.,* 110, 470 (1971).

[11] Katz, Z., et al, "Teratogenicity of Progestogens Given During the First Trimester of Pregnancy," *Obstet. Gynecol.* 65, 775 (1983); and Resseguie, L. J., et al, "Congenital Malformations Among Offspring, Exposed in Utero to Progestins, Olmsted County, Minn., 1936–1974," *Fertil. Steril.,* 43, 514 (1985).

[12] Mishell, D. R., "Absorption of Steroids Through Silastic in Animals and Humans—Results of Studies in Humans," *Advances in Planned Parenthood,* 5, 151 (1970).

[13] Sivin, I., et al. "A Multicenter Study of Levon-orgestrel-estradiol Contraceptive Vaginal Rings. I. Use Effectiveness. An International Comparative Trial," *Contraception,* 24, 341 (1981); Mishell, D. R., et al, Clinical Performances and Endocrine Profiles with Contraceptive Vaginal Rings Containing a Combination of Estradiol and D-Norgestrel," *Am. J. Obstet. Gynecol.,* 130, 55 (1978); Folkman, J., et al, "The Use of Silicone Rubber as a Carrier for Prolonged Drug Therapy," *J. Surg. Res.,* 4, 139 (1964); Toivonen, J., "Pituitary and Gonadal Function During the use of Progesterone- or Progesterone-estradiol-releasing Vaginal Rings," *Int. J. Fertil.,* 25, 106 (1980); Mischell, D. R. et al, "Inhibition of Ovulation with Cyclic Use of Progesten-Impregnated Intravaginal Devices," *Am. J. Obstet. Gynecol.,* 113 927 (1972); Johansson, E. D. B. et al. "The Effect of Progestin R2323 Released from Vaginal Rings on Ovarian Function," *Contraception,* 12 299 (1975); Mischell, D. R. et al, "Contraception By Means of a Silastic Vaginal Ring Impregnated With Medroxyprogesterone Acetate," *Contraception* 107, 100 (1970); Mishell, D. R., et al, "Contraceptive Effect of Varying Dosages of Progestogen in Silastic Vaginal Rings," *Fertil. Steril.* 21, 99 (1970); and Mischell, footnote 13, infra.

[14] Stumpf, P. G., et al, "Development of a Vaginal Ring for Achieving Physiologic Levels of 17b-estradiol in Hypoestrogenic Women," *J. Clin. Endocrinol. Metab.,* 54, 208 (1982).

[15] Yen, S. S. C., et al, "Circulating Estradiol, Estrone and Gonadotropin Levels Following the Administration of Orally Active 17b-estradiol in Postmenopausal Women,"*J. Clin. Endocrinol. Metab.,* 40, 518 (1975).

[16] Loeper, footnote 6, infra.

[17] Nora, A. H., et al, "A Syndrome of Multiple Congenital Anomalies Associated with Teratogenic Exposure," *Arch. Environ. Health,* 30, 17 (1975); See also Katz, et al and *Resseguie,* et al., footnote 12, infra.

[18] Landgren, B. M. et al., "Hormonal Profile of the Cycle in 68 Normally Menstruating Women," *Acta Endocrinologica* 94, 89 (1980).

[19] Csapo, *Am. J. Obstet. Gynecol.* 115, 759 (1973).

I claim:

1. A method for producing, in a functionally agonadal human female body, an environment suitable for the phases of preparation for implanation, nutrition, and development of an embryo, comprising:

placing a carrier containing at least one releasable naturally occurring human steroid hormone into the vagina of said female body, thereby producing normal serum steroid hormone levels within each of said phases.

2. The method of claim 1, wherein said carrier is a solid material.

3. The method of claim 1, wherein said carrier is a silicone elastomer.

4. The method of claim 1, wherein said carrier is a polysiloxane.

5. The method of claim 1, wherein said carrier is polyethylene glycol.

6. The method of claim 1, wherein said steroid hormone is a combination of 17-beta-estradiol and progesterone.

7. The method of claim 1, wherein said carrier is shaped like a ring.

8. The method of claim 1, wherein a ring-shaped carrier is utilized in combination with an additional carrier of cylindrical shape.

9. The method of claim 1 and further including the step of subsequently substituting said carrier with at least one other carrier containing a different amount of said steroid hormone.

10. A method for augmenting, in a human female body, inadequate natural steroid hormone levels thereby stimulating the steroid milieu of the normal human female ovulatory menstral cycle, comprising:

placing a silicone elastomer carrier containing at least one releaseable naturally occurring human steroid hormone into the vagina of said female body, thereby producing normal serum steroid hormone levels.

11. The method of claim 10, wherein said carrier is solid material.

12. The method of claim 10, wherein said carrier is is a polysiloxane.

13. The method of claim 10, wherein said steroid hormone is a combination of 17-beta-estradiol and progesterone.

14. The method of claim 10, wherein said carrier is shaped like a ring.

15. The method of claim 10, wherein a ring-shaped carrier is utilized in combination with an additional carrier of cylindrical shape.

16. The method of claim 10, and further including the step of substituting said carrier with at least one other carrier containing a different amount of said steroid hormone.

17. The method of claim 10, including the step of producing normal serum steroid hormone levels for the phases of implantation, nutrition, and development of an embryo.

18. A method for simulating the steroid milieu of the normal human female ovulatory menstral cycle in a functionally agonadal human female body, comprising:
placing a silicon elastomer carrier containing and releasing a steroid hormone selected from the group consisting of 17-β-estradiol, progesterone and the mixture of 17-β estradiol and progesterone into the vagina of said female body, thereby producing normal serum steroid hormone levels.

* * * * *